(12) United States Patent
Yang et al.

(10) Patent No.: US 8,889,927 B2
(45) Date of Patent: Nov. 18, 2014

(54) METHOD TO REDUCE THE FORMATION OF HIGH BOILING COMPOUNDS DURING THE DEHYDROCHLORINATION OF 1,1,1,3-TETRACHLOROPROPANE

(71) Applicant: Honeywell International Inc., Morristown, NJ (US)

(72) Inventors: Terris Yang, East Amherst, NY (US); Joshua Close, Blasdell, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 49 days.

(21) Appl. No.: 13/796,328

(22) Filed: Mar. 12, 2013

(65) Prior Publication Data

US 2014/0275658 A1  Sep. 18, 2014

(51) Int. Cl.
   *C07C 17/25* (2006.01)
   *C07C 21/04* (2006.01)
   *C07C 19/01* (2006.01)
   *C07C 17/269* (2006.01)

(52) U.S. Cl.
   CPC ............... *C07C 17/25* (2013.01); *C07C 21/04* (2013.01); *C07C 17/269* (2013.01); *C07C 19/01* (2013.01)
   USPC ............................ 570/227; 570/226; 570/257

(58) Field of Classification Search
   CPC ........ C07C 19/01; C07C 21/04; C07C 17/269
   USPC .......................................... 570/227, 226, 257
   See application file for complete search history.

(56) References Cited

U.S. PATENT DOCUMENTS

| | | | |
|---|---|---|---|
| 4,535,194 A | 8/1985 | Woodard | |
| 4,650,914 A | 3/1987 | Woodard | |
| 6,534,688 B2 | 3/2003 | Klausmeyer | |
| 2011/0237843 A1* | 9/2011 | Tung et al. | 570/151 |
| 2012/0142980 A1 | 6/2012 | Nappa et al. | |
| 2012/0142981 A1 | 6/2012 | Souda et al. | |

FOREIGN PATENT DOCUMENTS

| | | |
|---|---|---|
| JP | 2010229047 A | 10/2010 |
| JP | 2012097017 A | 5/2012 |
| WO | 2013022676 A1 | 2/2013 |

OTHER PUBLICATIONS

PCT ISR & Written Opinion issued in PCT/US2014/019794 dated Jun. 13, 2014.

* cited by examiner

*Primary Examiner* — Fereydoun G Sajjadi
*Assistant Examiner* — Medhanit Bahta
(74) *Attorney, Agent, or Firm* — Bruce O. Bradford

(57) ABSTRACT

This invention relates to a method to improve 1,1,3-trichloropropene (HCC-1240za) and/or 3,3,3-trichloropropene (HCC-1240zf) selectivity in the dehydrochlorination of 1,1,1,3-tetrachloropropane (HCC-250fb). In normal practice, $FeCl_3$ is used as the catalyst for the dehydrochlorination of HCC-250fb to produce 1,1,3-trichloropropene and/or 3,3,3-trichloropropene. Here the improvement comprises, using as the starting material, a mixture comprising HCC-250fb and Heavies generated from the reaction of $CCl_4$ and ethylene to produce HCC-250fb, wherein the Heavies comprise one or more tetrachloropentane isomers. These compounds reduce or eliminate the formation of unwanted high boiling compounds (HBCs).

14 Claims, 1 Drawing Sheet

METHOD TO REDUCE THE FORMATION OF HIGH BOILING COMPOUNDS DURING THE DEHYDROCHLORINATION OF 1,1,1,3-TETRACHLOROPROPANE

BACKGROUND OF THE INVENTION

The compound 1,1,3-trichloropropene is useful as a chemical intermediate in the formation of other commercially important compounds. See, for example, U.S. Patent Pub. No. 2012-0142980, the disclosure of which is hereby incorporated herein by reference.

SUMMARY OF THE INVENTION

This invention relates to a method to improve the selectivity to 1,1,3-trichloropropene and/or 3,3,3-trichloropropene by the catalytic dehydrochlorination of HCC-250fb, 1,1,1,3-tetrachloropropane. In normal practice, $FeCl_3$ is used as the catalyst for the dehydrochlorination of HCC-250fb to produce 1,1,3-trichloropropene and/or 3,3,3-trichloropropene. See, for example, US Patent Pub. No. 2012-0035402, the disclosure of which is hereby incorporated herein by reference.

It has been discovered that when using only $FeCl_3$ as the catalyst for the dehydrochlorination of 250fb, the reaction products often contain significant amounts of unwanted high boiling compounds ("HBCs") such as pentachlorocyclohexene and/or hexachlorocyclohexane species, in addition to the desired product, namely 1,1,3-trichloropropene and/or 3,3,3-trichloropropene. While not wishing to be bound by any theory, it is believed that the formation of these HBCs is due to the dimerization of the reaction products, which can include the propene isomers, 1,1,3-trichloropropene and/or 3,3,3-trichloropropene. The formation of these HBCs reduces the selectivity to the desired product, 1,1,3-trichloropropene and/or 3,3,3-trichloropropene.

In the synthesis of HCC-250fb (hereafter the "step 1" process), HCC-250fb is produced from $CCl_4$ and ethylene with catalysts under certain reaction conditions. The catalysts used in the reaction are removed from the crude HCC-250fb product by distillation (Catalyst Recycle Column or CRC). Then, the "top" stream from CRC is fed to a lights distillation column to remove unreacted $CCl_4$ and ethylene. The "bottom" stream (namely HCC-250fb+Heavies) of the lights column is then fed into a third distillation column with pure HCC-250fb collected from the "top" stream. Typically, the pure HCC-250fb is then used as the raw material in a dehydrochlorination process to make 1,1,3-trichloropropene and/or 3,3,3-trichloropropene (hereafter the "step 2" process).

The present invention is based upon the discovery that the crude "bottom" stream from the step 1 process, which comprises a mixture of HCC-250fb and "Heavies" from the lights distillation column in the step 1 process, can be used as the raw material for the dehydrochlorination process to make 1,1,3-trichloropropene and/or 3,3,3-trichloropropene; and when this crude starting material was used, the formation of HBCs was significantly suppressed or eliminated.

Further analysis has found that, as byproducts from the step 1 reaction, one or more tetrachloropentane isomers, such as 1,1,1,5- and 1,3,3,5-tetrachloropentane, are present in the crude mixture of HCC-250fb+Heavies. These compounds are believed to play a role regarding both HCC-250fb conversion and HBC selectivity. In addition, certain trichloropentene isomers are produced by the dehydrochlorination of these tetrachloropentane isomers. These compounds can also inhibit the formation of HBCs. See the data shown in FIGS. 1 and 2.

Thus, one embodiment of the present invention is directed to a process for the dehydrochlorination of HCC-250fb to produce 1,1,3-trichloropropene and/or 3,3,3-trichloropropene using as the starting material, a crude mixture of HCC-250fb+Heavies generated from the step 1 process. As described above, certain of the Heavies included in this composition comprise tetrachloropentane isomers, such as 1,1,1,5-tetrachloropentane and/or 1,3,3,5-tetrachloropentane.

Thus, another embodiment of the present invention is directed to a process for the dehydrochlorination of HCC-250fb to produce 1,1,3-trichloropropene and/or 3,3,3-trichloropropene using as the starting material, a mixture of HCC-250fb and one or more tetrachloropentane isomers, such as 1,1,1,5- and 1,3,3,5-tetrachloropentane.

Thus, one embodiment of the present invention is directed to a process for the dehydrochlorination of HCC-250fb to produce 1,1,3-trichloropropene and/or 3,3,3-trichloropropene using as the starting material, a mixture of HCC-250fb and one or more trichloropentene isomers.

Thus, one embodiment of the present invention is directed to a process for the dehydrochlorination of HCC-250fb+Heavies to produce 1,1,3-trichloropropene and/or 3,3,3-trichloropropene using one or more metal halides or mixtures, such as $FeCl_3$ and/or $FeCl_2$, as the catalyst.

DETAILED DESCRIPTION OF THE INVENTION

Figure 1:
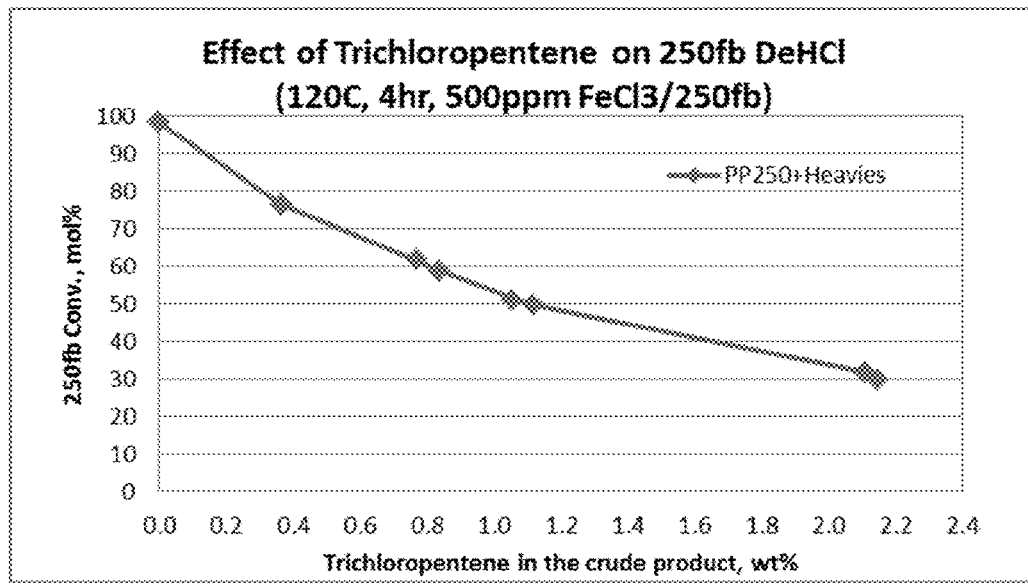
FIG. 1 shows the effect of trichloropentene isomers on HCC-250fb conversion in HCC-250 dehydrochlorination.
Figure 2:
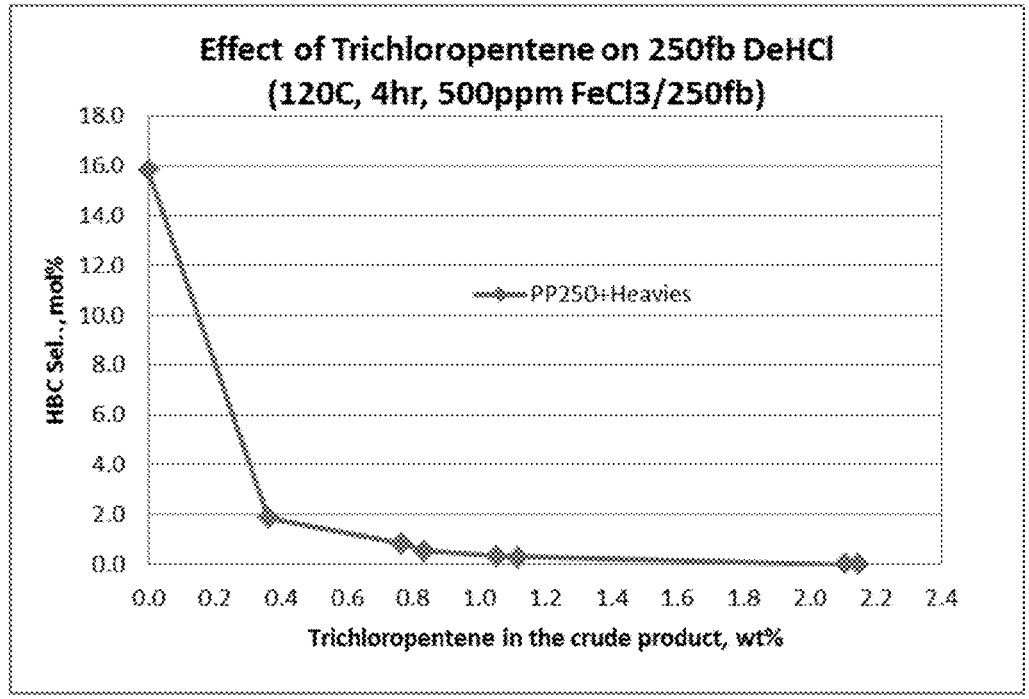
FIG. 2 shows the effect of trichloropentene isomers on HBC selectivity in HCC-250 dehydrochlorination.

As described above, it has been discovered that by using HCC-250fb+Heavies from the step 1 process as the starting material, the HCC-250 dehydrochlorination process can be conducted with significant reduction or elimination of unwanted HBCs, together with significantly improvement in the selectivity to the target products (1,1,3-trichloropropene and/or 3,3,3-trichloropropene). This improved selectivity is beneficial to the reduction of process waste and it simplifies the future separation of crude product for the combined step 1 and step 2 process reactions, and therefore reduces the overall production costs.

The catalytic HCC-250fb dehydrochlorination reaction is preferably carried out under conditions to attain a starting material conversion of at least about 20% or higher, preferably at least about 40% or higher, and even more preferably at least about 60% or higher, and a desired product 1,1,3-trichloropropene and/or 3,3,3-trichloropropene selectivity of at least about 50% or higher, preferably at least about 70% or higher, and more preferably at least about 95% or higher. Selectivity is calculated by the number of moles of product formed divided by the number of moles of reactant consumed.

Useful reaction temperatures for the catalytic dehydrochlorination reaction may range from about 50° C. to about 300° C. Preferred temperatures may range from about 70° C. to about 150° C., and more preferred temperatures may range from about 100° C. to about 125° C. One especially preferred reaction temperature is about 120° C. The reaction may be conducted at atmospheric pressure, super-atmospheric pressure or under vacuum. The vacuum pressure can be from about 0 torr to about 760 torr. Contact time of the reactant starting materials with the catalyst mixture may range from about 0.5 to 10 hours, preferably from about 2 to 8 hours, more preferably about 4 hours, however, longer or shorter times can be used.

EXAMPLE 1 (COMPARATIVE EXAMPLE)

A 500 ml glass flask (reactor) equipped with a magnetic stirring bar and a total condenser was charged with 100.6 g HCC-250fb (Honeywell, 99.8 wt %) and 0.029 g $FeCl_3$. The reactor was stirred and heated to 120°±2° C. via an oil bath. After 4 hours, the reactor was removed from the oil bath and cooled down to room temperature. Then the mixture in the reactor was filtered, washed with D.I. water and dried with $MgSO_4$. By GC analysis, the reaction mixture contained 73.3 wt % of 1,1,3-trichloropropene, 1.9 wt % of HCC-250fb and 24.6 wt % of HBCs, representing a HCC-250fb conversion of 98.3 mol %, 1,1,3-trichloropropene selectivity of 84.2 mol %, and HBCs selectivity of 15.8 mol %.

EXAMPLE 2

100.3 g HCC-250fb+Heavies from step 1 process (Honeywell, 98.3 wt %) and 0.025 g $FeCl_3$ were charged into the reactor with the same reaction conditions and procedure followed as described in Example 1. By GC analysis, the reaction mixture contained 34.2 wt % of 1,1,3-trichloropropene and 64.0 wt % of HCC-250fb with no HBCs detected, representing a HCC-250fb conversion of 40.1 mol %, 1,1,3-trichloro-propene selectivity of 100.0 mol % and HBCs selectivity of 0.0 mol %.

EXAMPLE 3

100.8 g HCC-250fb+Heavies from step 1 process (Honeywell, 98.3 wt %) and 0.126 g $FeCl_3$ were charged into the reactor with the same reaction conditions and procedure followed as described in Example 1. By GC analysis, the reaction mixture contained 69.6 wt % of 1,1,3-trichloropropene, 24.9 wt % of HCC-250fb and 2.5 wt % of HBCs, representing a HCC-250fb conversion of 78.2 mol %, 1,1,3-trichloropropene selectivity of 96.8 mol % and HBCs selectivity of 3.2 mol %.

EXAMPLE 4

The same apparatus as described in Example 1 was charged with 100.4 g HCC-250fb+Heavies (Honeywell, 98.0 wt %) and 0.107 g $FeCl_3$. The same reaction conditions and procedure were followed as in Example 1 except for the reaction temperature was controlled at 100°±2° C. and the residence time was 2 hours. By GC analysis, the reaction mixture contained 51.4 wt % of 1,1,3-trichloropropene, 45.8 wt % of HCC-250fb and 1.0 wt % of HBCs, representing a HCC-250fb conversion of 58.6 mol %, 1,1,3-trichloropropene selectivity of 99.0 mol % and HBCs selectivity of 1.0 mol %.

EXAMPLE 5

The same apparatus as described in Example 1 was charged with 100.0 g HCC-250fb+Heavies (Honeywell, 98.0 wt %) and 0.101 g $FeCl_3$. The same reaction conditions and procedure were followed as in Example 1 except for the reaction temperature was controlled at 80°±2° C. By GC analysis, the reaction mixture contained 52.1 wt % of 1,1,3-trichloropropene, 44.6 wt % of HCC-250fb and 1.9 wt % of HBCs, representing a HCC-250fb conversion of 59.6 mol %, 1,1,3-trichloropropene selectivity of 98.1 mol % and HBCs selectivity of 1.9 mol %.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. In the process of the catalytic dehydrochlorination of 1,1,1,3-tetrachloropropane (HCC-250fb) to produce 1,1,3-trichloropropene and/or 3,3,3-trichloropropene, the improvement comprising, using as the starting material, a mixture comprising HCC-250fb and Heavies generated from the reaction of $CCl_4$ and ethylene to produce HCC-250fb, wherein the Heavies comprise one or more tetrachloropentane isomers wherein the dehydrochlorination catalyst comprises one or more metal halides or mixtures thereof and the dehydrochlorination reaction temperature ranges from 50 to 140° C.

2. The process of claim 1, wherein the dehydrochlorination catalyst comprises $FeCl_3$ and/or $FeCl_2$.

3. The process of claim 2, wherein the dehydrochlorination reaction temperature can range from, but preferably 80° to 120° C.

4. The process of claim 2, wherein the dehydrochlorination reaction time can range from 0.5 to 10 hours.

5. The process of claim 2, wherein the dehydrochlorination reaction time can range from 1 to 4 hours.

6. The process of claim 2, wherein the weight ratio of the catalyst to the reactant 1,1,1,3-tetrachloropropane can range from above 0 to 5% by weight.

7. The process of claim 2, wherein the weight ratio of the catalyst to the reactant 1,1,1,3-tetrachloropropane can range from 0.01% to 0.5% by weight.

8. The process of claim 2, wherein the concentration of tetrachloropentane isomers in HCC-250fb+Heavies range from 0.001% to 5% by weight.

9. The process of claim 2, wherein the concentration of tetrachloropentane isomers in HCC-250fb+Heavies range from 0.1% to 2% by weight.

10. The process of claim 2, wherein the concentration of tetrachloropentane isomers in HCC-250fb+Heavies range from 0.3% to 1.0% by weight.

11. A process for the catalytic dehydrochlorination of HCC-250fb to produce 1,1,3-trichloropropene and/or 3,3,3-trichloropropene, comprising dehydrochlorinating HCC-250fb using metal halide catalyst at a temperature from 50° to 140° C. and reaction time from 0.5 to 10 hours; wherein the dehydroclorination process includes one or more tetrachloropentane isomers.

12. The process of claim 11, wherein the tetrachloropentane isomers comprise 1,1,1,5-tetrachloropentane.

13. The process of claim 11, wherein the tetrachloropentane isomers comprise 1,3,3,5-tetrachloropentane.

14. A process for the catalytic dehydrochlorination of HCC-250fb to produce 1,1,3-trichloropropene and/or 3,3,3-trichloropropene, comprising dehydrochlorinating HCC-250fb using metal halide catalyst at a temperature from 50° to 140° C. and reaction time from 0.5 to 10 hours; wherein the dehydroclorination process includes one or more trichloropentene isomers.

* * * * *